US008842281B2

(12) United States Patent
Ruffin et al.

(10) Patent No.: US 8,842,281 B2
(45) Date of Patent: Sep. 23, 2014

(54) SYSTEM AND METHOD FOR DETECTING THE AMOUNT OF STABILIZER DEGRADATION IN SOLID ROCKET PROPELLANT

(75) Inventors: Paul B. Ruffin, Harvest, AL (US); Eugene Edwards, Huntsville, AL (US); Christina L. Brantley, Huntsville, AL (US); Fang Luo, State College, PA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 242 days.

(21) Appl. No.: 13/553,104

(22) Filed: Jul. 19, 2012

(65) Prior Publication Data

US 2014/0022551 A1   Jan. 23, 2014

(51) Int. Cl.
*G01N 21/59* (2006.01)
*G01N 21/31* (2006.01)

(52) U.S. Cl.
CPC ............ *G01N 21/59* (2013.01); *G01N 21/3151* (2013.01)
USPC .............................. 356/436; 356/70; 356/326

(58) Field of Classification Search
CPC .......... G01N 21/1702; G01N 21/3563; G01N 21/7703; G01N 33/26; G01N 33/22; B64G 1/401; B64G 1/403; F02K 9/96; G01J 3/0218; G01J 3/42; G01J 3/443; G01M 15/14

USPC .................................... 356/432–440, 326, 70
See application file for complete search history.

(56) References Cited

U.S. PATENT DOCUMENTS

| | | | | |
|---|---|---|---|---|
| 5,691,701 A * | 11/1997 | Wohlstein et al. | ............ | 340/603 |
| 6,240,305 B1 * | 5/2001 | Tsuchiya | ....................... | 600/310 |
| 6,530,213 B2 * | 3/2003 | Beck et al. | ....................... | 60/204 |
| 6,762,841 B1 * | 7/2004 | Bragg et al. | .................. | 356/436 |
| 7,312,452 B2 * | 12/2007 | Klingenberg et al. | ... | 250/339.13 |
| 7,599,065 B2 * | 10/2009 | Sendai | ......................... | 356/432 |
| 8,009,294 B2 | 8/2011 | Shpantzer et al. | | |
| 2010/0171956 A1 * | 7/2010 | Sappey et al. | ................. | 356/432 |
| 2013/0224872 A1 * | 8/2013 | Brantley et al. | ............... | 436/117 |

* cited by examiner

*Primary Examiner* — Hoa Pham
(74) *Attorney, Agent, or Firm* — William Bradley Haymond

(57) ABSTRACT

A spectrometric system, including: a solid rocket fuel; an illuminating source including at least two wavelengths within a spectral range from 100 nm to 200,000 nm, a first wavelength or range of wavelengths having a distinguishably greater or lesser absorbance for the stabilizer than for components of the propellant, and a second wavelength or range of wavelengths having an absorbance for the stabilizer not distinguishably different than the absorbance for the components of the propellant, an illuminating fiber to illuminate a surface of a solid rocket fuel; a collecting fiber to collect back scattered, reflected or transmitted light being given off from the surface of the solid rocket fuel; and a spectrometer to determine the light intensities of the two wavelengths of the back scattered, reflected or transmitted light collected.

20 Claims, 13 Drawing Sheets

SYSTEM AND METHOD FOR DETECTING THE AMOUNT OF STABILIZER DEGRADATION IN SOLID ROCKET PROPELLANT

BACKGROUND

Solid fuels are widely used as propellants in missile engines. The burning of the fuels generates a huge thrust so that a missile can be quickly launched. The main chemical components of solid fuels include nitrocellulose, nitroglycerin, carbon (C), and sulfur (S). Such fuels are usually stored in the back portion of the missile for effectively generating the thrust. A stabilizer is used with the fuel composition to slow the chemical degradation process among the different components of the fuel during the long storage process.

BRIEF DESCRIPTION OF THE DRAWINGS

Features and advantages of embodiments of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

During the long storage process of missiles (e.g., years), stabilizer, such as MNA or BUN, significantly slows the chemical degradation process among the different components of the solid rocket fuel (e.g. double base fuel), thus slowing the aging process, which slowing in turn results in the continued effectiveness of the fuel over a longer period. Therefore, the presence of the stabilizer helps preserve the fuel. Without the stabilizer, the solid rocket fuel lasts for a noticeably shorter time. However, in normal circumstances, over time, the stabilizer itself reacts with components of the propellant and is gradually degraded and consumed with the propellant components. The degradation and consumption of the stabilizer causes it to lose its effectiveness in preventing degradation of the solid rocket fuel. Once the concentration level of the stabilizer is below certain threshold levels, the fuel is no longer safe or effective to use due to the degradation of the various fuel components. Thus, the concentration level of stabilizer can be used as an indicator of the health of the fuel. To monitor the effectiveness of the solid rocket fuel and to help ensure a successful and safe launch of the missile, the fuel can be tested beforehand for sufficient concentration of non-degraded stabilizer, such as MNA or BTTN. A sufficient concentration of non-degraded stabilizer is a dependable indicator that the solid rocket fuel in the missile is currently effective. Lack of a sufficient concentration of non-degraded stabilizer indicates that, not only is sufficient stabilizer lacking in the fuel, but more significantly that the solid rocket propellant components have themselves degraded and lost effectiveness.

Figure 1:
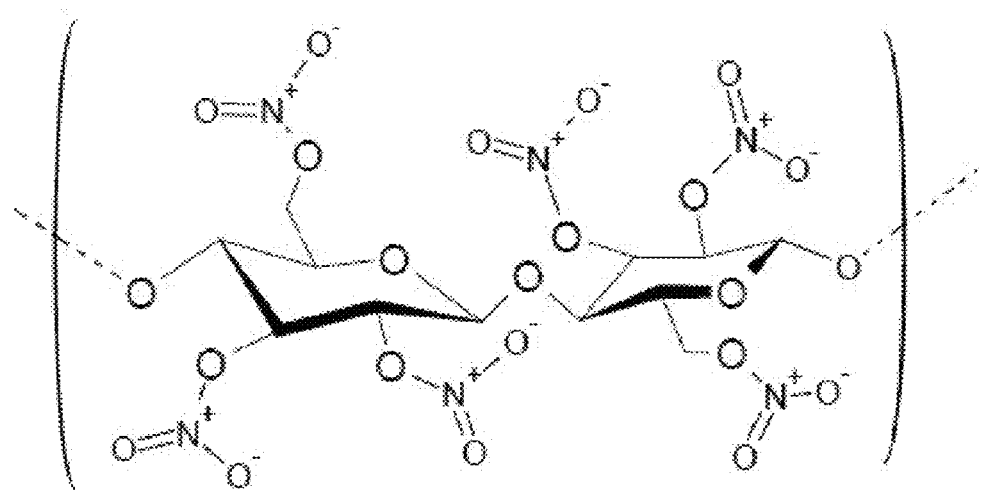
FIG. 1 is a drawing illustrating the molecular structure of Nitrocellulose (NC): $C_6H_7(NO_2)_3O_5$ of the double-base Nitrocellulose/Nitroglycerin (NC/NG) propellant (M9).
Figure 2:
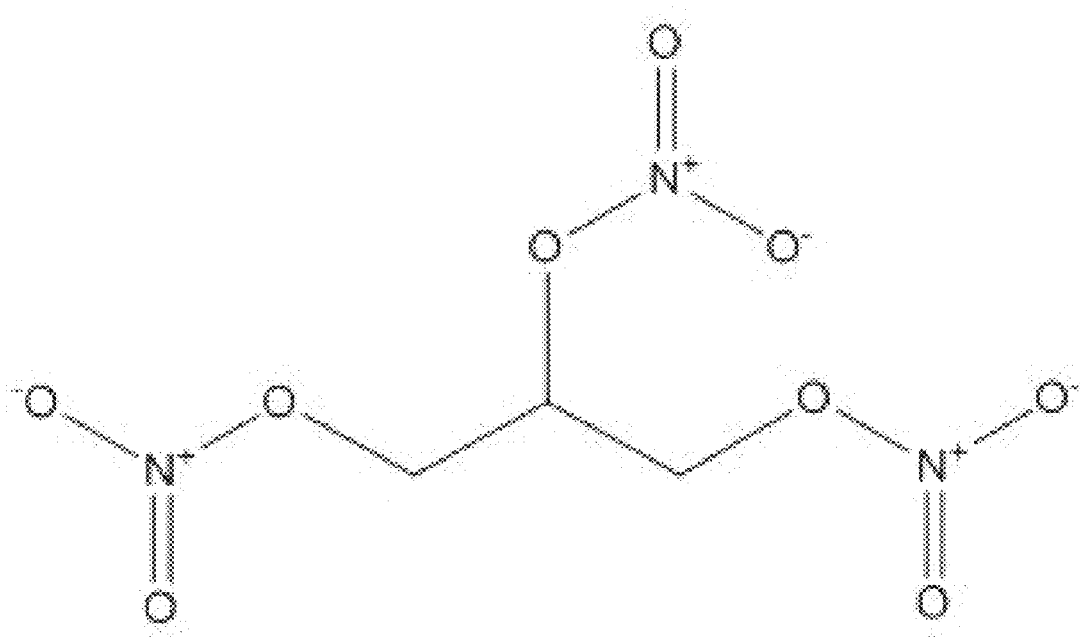
FIG. 2 is a drawing illustrating the molecular structure of Nitroglycerin (NG): $C_3H_5N_3O_9$ of the double-base NC/NG propellant (M9).

Nitrate-ester propellants have been widely used as low emission, solid state fuels. One example of a nitrate-ester propellant is the double-base NC/NG solid state propellant, M9. The molecular structure of NC and NG are illustrated in FIGS. 1 and 2, respectively. In one example studied, the M9 nitrate-ester propellant sample had a composition of: 57.75 wt % NC, 40 wt % NG, 0.75 wt % ethyl cellulose (EC), and 1.50 wt % $KNO_3$. Under normal circumstances, when it is actually used in a rocket, M9 often also contains small amounts of carbon black. In another example, an alternative double-base nitrate-ester propellant which can be used is Nosih-AA2 minimum smoke double base propellant (MK90), which includes no carbon black.

Figure 3:
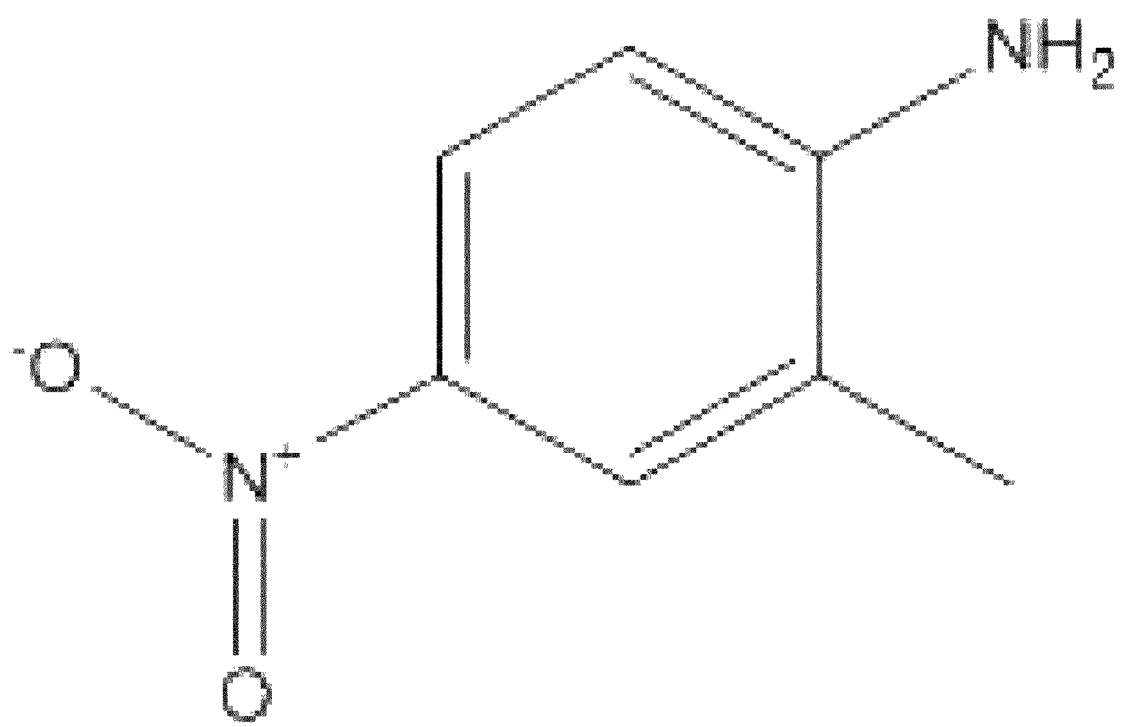
FIG. 3 is a drawing illustrating the molecular structure of stabilizer 2-methyl-4-nitroaniline (MNA): $C_7H_8N_2O_2$.

MNA is an often-used stabilizer with M9 nitrate-ester propellants. The chemical structure of MNA is shown in FIG. 3. Alternatively, BTTN is another similarly effective stabilizer that can be used with some nitrate-ester propellants, such as MK90, which do not contain carbon black.

Figure 4:
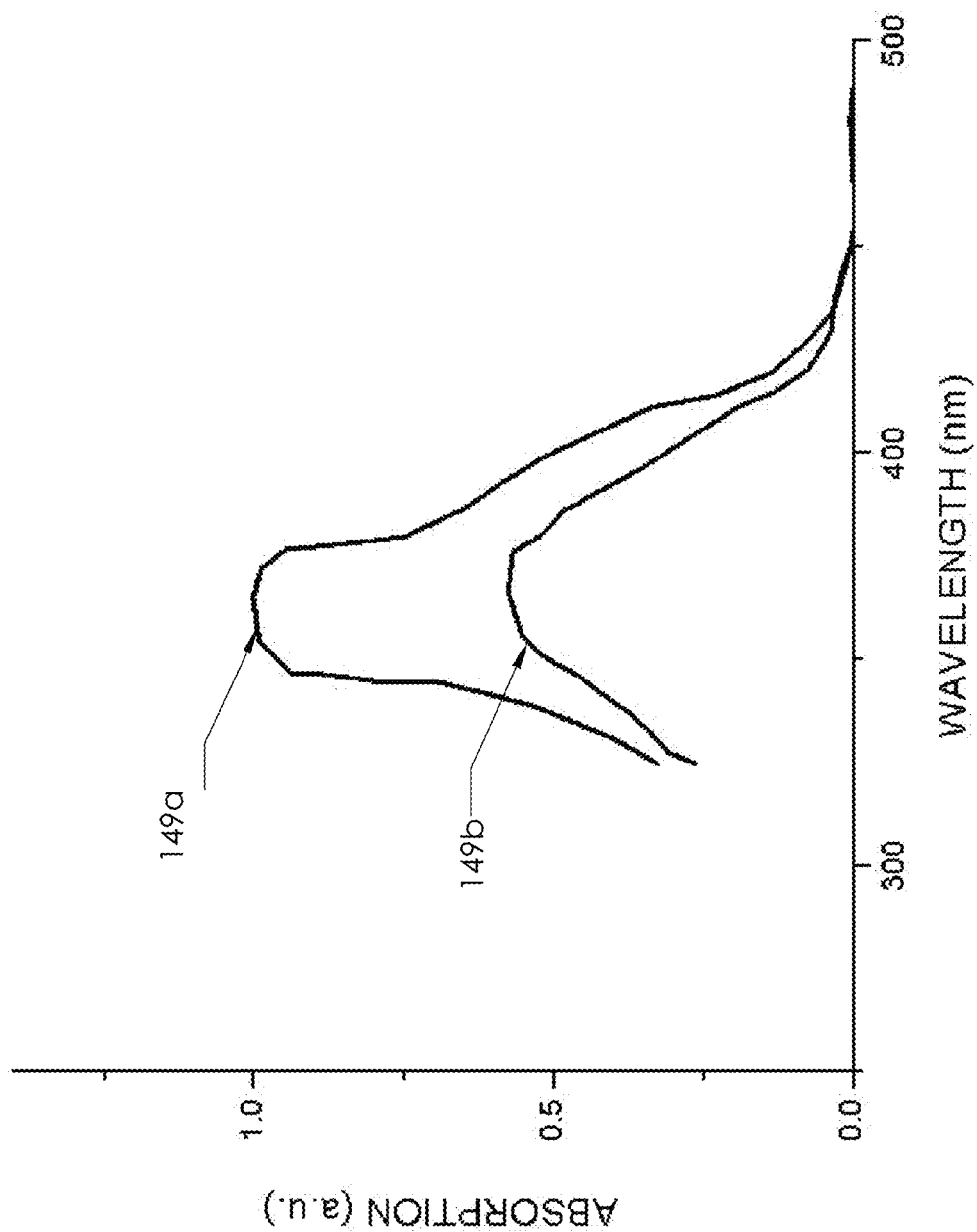
FIG. 4 is a drawing of the UV/blue absorption spectra of poled and unpoled MNA.

MNA has a strong absorption in the UV/blue spectral region (i.e., in the range between approximately 450 and 490 nm, especially around 473 nm), as shown in FIG. 4. As a chromophore polymer, MNA can spontaneously align, or "pole", when the polymer is near its glass transition temperature ($T_g$). It has been found that MNA strongly absorbs light in the UV/blue spectral range in both the poled form and unpoled form. As shown in FIG. 4, the poled MNA peak 149a indicating absorption (approximately 0.5 a.u.) in the UV/blue spectral range is approximately only half of the area of the unpoled MNA peak 149b also indicating absorption (approximately 1.0 a.u.) in the UV/blue spectral range.

The absorption coefficient for MNA in the UV/blue spectral range is noticeably larger than the absorption coefficients of the components of M9 nitrate-ester propellant, which include NC, NG, and oftentimes carbon black. Based on this fact, it is possible to determine the concentration level of MNA, and thus the amount of its degradation, by measuring the back scattered, reflection, or transmission light spectra of MNA along with the accompanying M9 nitrate-ester propellant components. The MNA and the M9 components' spectra are measured within the UV/visible/IR spectral range. The larger the absorption of MNA in this UV/blue spectral range, (i.e. around 473 nm), the lower the signal intensity shown by the spectrometer. When such a low signal intensity is shown, it follows that the concentration level of MNA will be higher. In comparison, the other components of the M9 nitrate-ester propellant composition do not have such a pronounced absorption in the UV/blue spectral range and therefore do not exert such an absorption effect on the signal intensity reading. When the light intensity is measured at certain other chosen wavelength ranges (e.g., green or red), an absorption effect from MNA is not noticeable. MNA absorption is not distinguishable at all in comparison to the amount of the absorption of the other components of the M9 nitrate-ester propellant composition, including NC, NG, and carbon black, even when the absolute concentration level of MNA in the propellant is relatively high in comparison to conventional amounts of stabilizer in the propellant. Therefore, the signal intensity in this comparative reading, without the specific absorption of MNA in the UV/blue spectral range, is noticeably higher. It can be seen that these qualities of MNA in comparison to the other propellant components occur because of the MNA stabilizers' notable absorption properties at blue wavelengths around 473 nm. Thus, for example, one can determine the concentration levels of MNA in M9 nitrate-ester propellant by measuring the light intensity of MNA in M9 nitrate-ester propellant at blue spectral range and, for comparison, by measuring the light intensity of MNA in M9 nitrate-ester propellant at at least one other color of the UV/visible/IR spectral range, such as green or red.

An embodiment of a method for determining the amount of stabilizer degradation is the measurement of light intensity from at least two spectral regions, e.g., the UV/blue spectral region and the green spectral region, when light is passed through a portion of the rocket fuel. Such a method can be used with a spectrometer to measure MNA/M9 nitrate-ester propellant light intensity in at least one of the following forms: a backscattered light spectra, a reflection light spectra and a transmission light spectra.

It has been found that there are other wavelengths, besides the exemplified blue and green, at which the absorbance of stabilizer, such as MNA or BTTN, is quite distinctly different than the absorbance of propellant components such as NC, NG and carbon black within which the stabilizer is mixed. Thus, although blue and green wavelengths can be used to obtain this effect with MNA by measuring the light intensity of both MNA and its propellant components, the same effect can be found for both MNA and BTTN with other empirically-determined wavelengths between 100 nm and 200,000 nm. Thus generally, if the choice of wavelengths is not limited to blue and green wavelengths, one can choose two other specific wavelengths or ranges of wavelengths in order to be able to determine the concentration of stabilizer in the propellant. One of these chosen wavelengths or ranges of wavelengths needs to consistently provide a distinguishably different (i.e., distinguishably larger or smaller) absorption for the stabilizer in comparison to its absorption for the propellant component materials which accompany the stabilizer. Just as consistently, the other of the two chosen wavelengths should not produce any such distinguishable difference in absorptions between the stabilizer and the propellant components.

Figure 5:
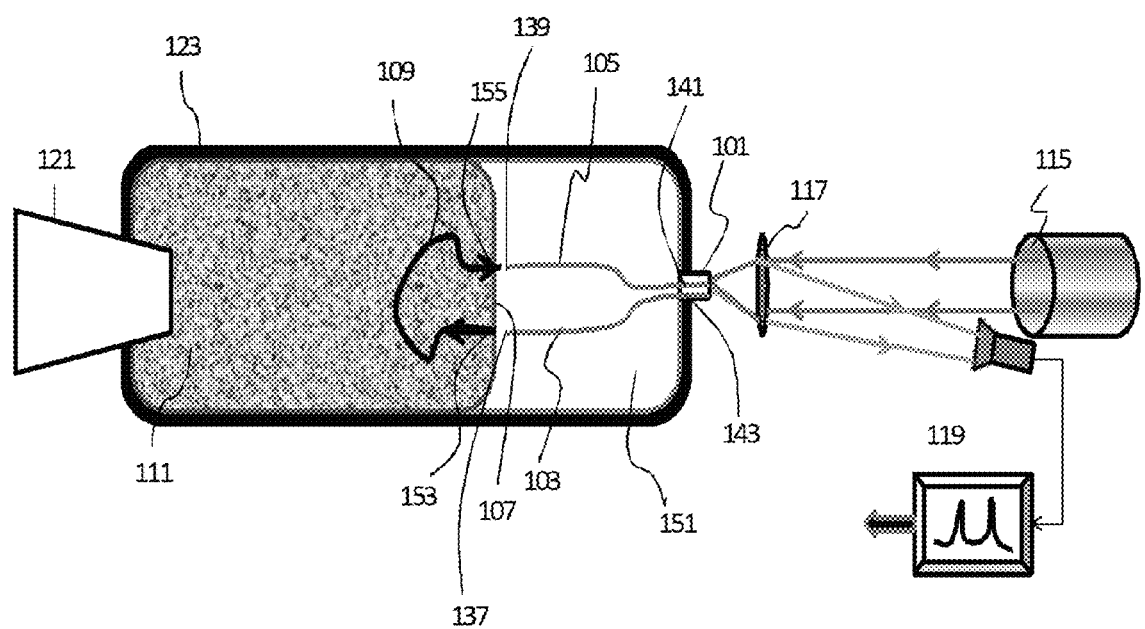
FIG. 5 is a conceptual drawing of a fiber optic, back scattered light spectroscopic system used for measuring the light intensity of the stabilizer back scattered light spectra.

One embodiment of a method of the present application is based on measuring the back scattered light spectra. FIG. 5 is a conceptual drawing of a scheme that can be used for detecting the back scattered light spectra in this embodiment. In FIG. 5 is shown an optical port 101 which is situated in the metal shell 123 covering the solid rocket fuel 111, the optical port 101 being on the end of the metal shell 123 opposite from the nozzle 121. The optical port 101 accesses a space 151 within the metal shell 123 in which a propellant surface 107 is accessible to optical fibers. Through the optical port 101 are strung two optical fibers: an illuminating fiber 103 and a collecting fiber 105. The light in the illuminating fiber 103 originates from a UV-visible light source 115 and travels through a light-directing device 117 (e.g., a lens) and into the illuminating fiber light-entering end 143, through the illuminating fiber 103 as it passes from the orbital port 101 and through the space 151, and out the illuminating fiber light-exiting end 137. The light from the illuminating fiber 103 includes light having at least two wavelengths within a spectral range from 100 nm to 200,000 nm wavelengths, a first wavelength or range of wavelengths producing a distinguishably different (i.e. either greater or lesser) light absorbance for the stabilizer than for components of the propellant, and a second wavelength or range of wavelengths producing a light absorbance for the stabilizer not distinguishably different than for the components of the propellant. Both the illuminating fiber light-exiting end 137 and the collecting fiber light-entering end 139 are in contact with or are in close proximity to, but do not penetrate, the propellant surface 107 in the space 151 in the metal shell 123. The light from the illuminating fiber light-exiting end 137 contacts a light-contacting portion 153 of the propellant surface 107 and the light penetrates into the solid rocket fuel 111. After the light penetrates into the solid rocket fuel 111, the light back scatters randomly around an area beneath the propellant surface 107 to form internal back scattered light 109. The internal back scattered light 109 finds its way out again at a light-collecting portion 155 of the propellant surface 107. The collecting fiber light-entering end 139 collects the internal back scattered light 109 emerging at the light-collecting portion 155 of the propellant surface 107. Both the light-contacting portion 153 and the light-collecting portion 155 are chosen, based not on any unique chemical or physical qualities in comparison to the rest of the surface 107, but rather because of their specific positions for the illuminating fiber light-exiting end 137 to access and shine light on the light-contacting portion 153 and for the collecting fiber light-exiting end 141 to access the light-collecting portion 155 and collect the internal back scattered light 109. The light travels along the collecting fiber 105, as the collecting fiber 105 passes into the optical port 101, to the collecting fiber light-exiting end 141. From the collecting fiber light-exiting end 141, the light passes back through the light directing device 117 (e.g. a lens) and into a UV-visible spectrometer 119 which measures the UV-visible back scattered light spectra. When the light from the light directing device 117 enters the UV-visible spectrometer 119, the spectrometer shows the light intensity of the back scattered light spectra of the stabilizer MNA along with the other components of the M9 nitrate-ester propellant material in the solid rocket fuel 111.

Figure 6:
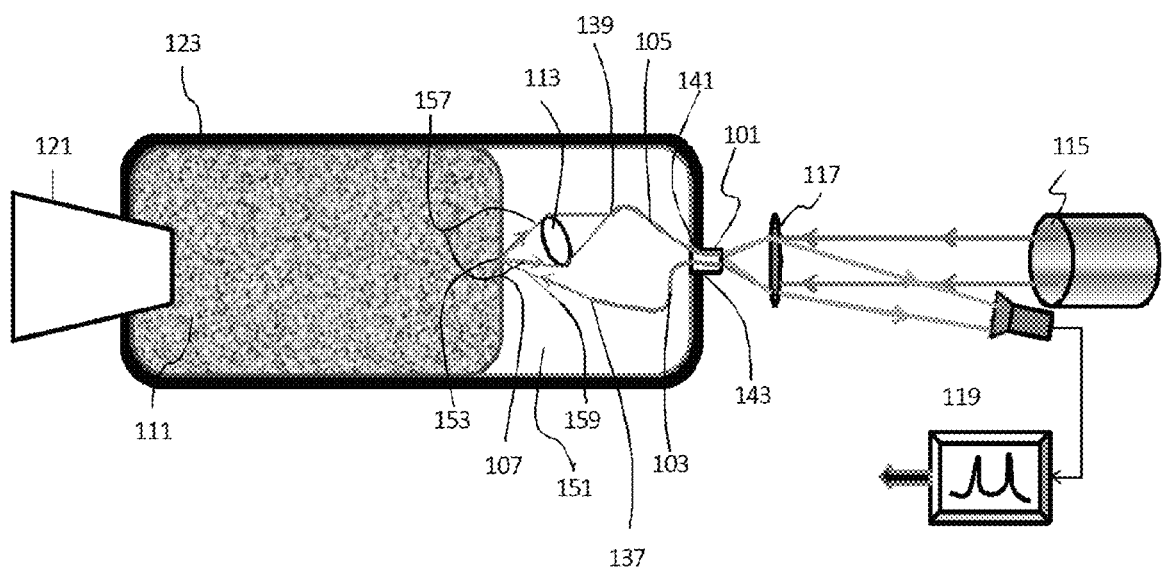
FIG. 6 is a conceptual drawing of a fiber optic, reflection light spectroscopic system used for measuring the light intensity of the stabilizer reflection light spectra.

A second embodiment of the method is based on measuring the reflection light spectra. FIG. 6 is a conceptual drawing of a scheme that can be used for detecting the reflection light spectra in this embodiment. The UV visible light source 115 beams a light through a light directing device 117 (e.g., a lens) and into an illuminating fiber light-entering end 143 of an illuminating fiber 103. The illuminating fiber 103 is strung through an optical port 101 situated on the metal shell 123 covering the solid rocket fuel 111, the optical port 101 being opposite from the nozzle 121. The optical port 101 accesses a space 151 within the metal shell 123 in which a propellant surface 107 is accessible to optical fibers. The light, having travelled through the illuminating fiber light-entering end 143, travels along the illuminating fiber 103, as it passes from the optical port 101 and through the space 151, to the illuminating fiber light-exiting end 137. The light from the illuminating fiber 103 includes light having at least two wavelengths within a spectral range from 100 nm to 200,000 nm wavelengths, a first wavelength or range of wavelengths producing a distinguishably different (i.e. either greater or lesser) light absorbance for the stabilizer than for components of the propellant, and a second wavelength or range of wavelengths producing a light absorbance for the stabilizer not distinguishably different than for the components of the propellant. In measuring the reflection light spectra, the illuminating fiber light-exiting end 137 does not contact the surface 107 but maintains a distance from the surface 107. The to-be-reflected light 159 exits from the illuminating fiber light-exiting end 137 and contacts a light-contacting portion 153 of the propellant surface 107. Reflected off of the propellant surface 107 is a reflected light 157 which is reflected from the light-contacting portion 153 without appreciably penetrating into the solid rocket fuel 111. The reflected light 157 from the light-contacting portion 153 of the propellant surface 107 reflects to and is collected by a light-collecting device 113 (e.g., a lens, a mirror, or an integration sphere). The light-contacting portion 153 is chosen, based not on any unique chemical or physical qualities in comparison to the rest of the surface 107, but rather because of its convenient position for the illuminating fiber light-exiting end 137 and the light-collecting device 113 to access the light-contacting portion 153. For detecting the reflection light spectra, the light-collecting device 113 collects the reflected light 157 from multiple directions as the reflected light 157 is reflected off of the light-contacting portion 153 of the propellant surface 107. The collected light from the light-collecting device 113 is then directed into the collecting fiber light-entering end 139. The light travels along inside the collecting fiber 105, as the collecting fiber 105 passes into the optical port 101, to the collecting fiber light-exiting end 141. The collecting fiber light-exiting end 141 directs light back through the light directing device 117. The light directed from the light directing device 117 enters a UV/visible spectrometer 119 that measures the reflection light spectra of the reflected light 157. When the light from the light directing device 117 enters the UV-visible spectrometer 119, the spectrometer shows the light intensity of the reflection light spectra of the stabilizer MNA along with the other components of the M9 nitrate-ester propellant material in the solid rocket fuel 111.

Figure 7:
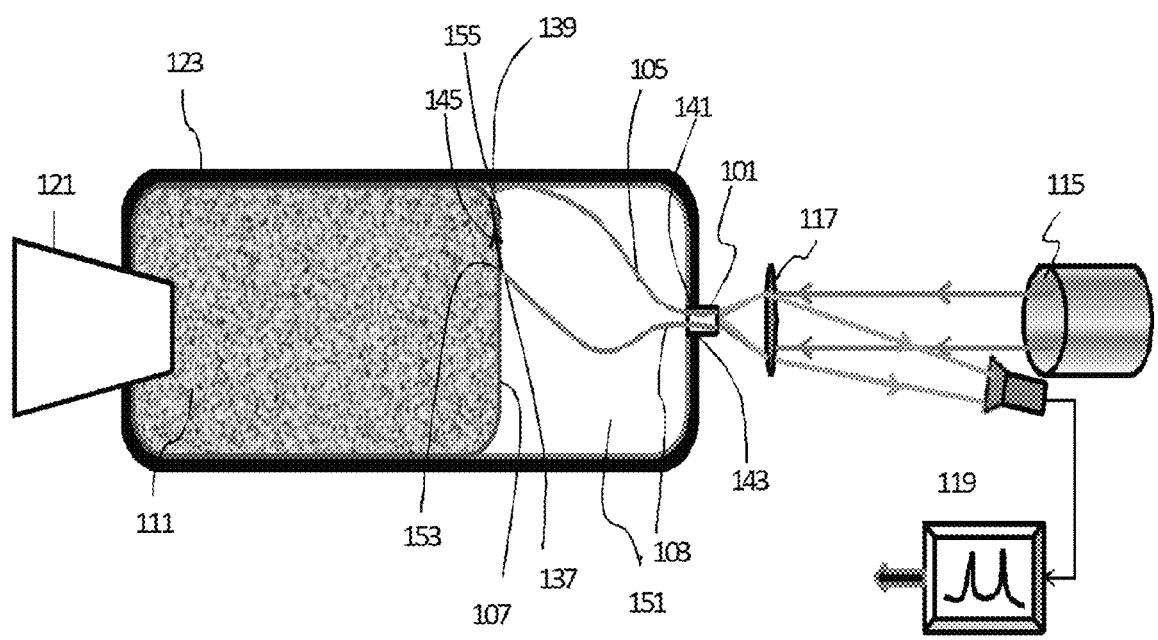
FIG. 7 is a conceptual drawing of a fiber optic, transmission light spectroscopic system used for measuring the light intensity of the stabilizer transmission light spectra.

Finally, a third embodiment of the method is based on measuring the transmission light spectra. FIG. 7 is a conceptual drawing of a scheme that can be used for detecting the transmission light spectra in this embodiment. In this scheme, the UV visible light source 115 beams a light through a light directing device 117 (e.g., a lens) and then into an illuminating fiber light-entering end 143. The illuminating fiber 103 is strung through an optical port 101 situated on the metal shell 123 covering the solid rocket fuel 111, the optical port 101 being opposite the nozzle 121. The optical port 101 accesses a space 151 within the metal shell 123 in which a propellant surface 107 is accessible to optical fibers. The light, having travelled through the illuminating fiber light-entering end 143, travels through the illuminating fiber 103, as the illuminating fiber 103 passes from the orbital port 101 and through the space 151, to the illuminating fiber light-exiting end 137. The light from the illuminating fiber 103 includes light having at least two wavelengths within a spectral range from 100 nm to 200,000 nm wavelengths, a first Wavelength or range of wavelengths producing a distinguishably different (i.e. either greater or lesser) light absorbance for the stabilizer than for components of the propellant, and a second wavelength or range of wavelengths producing a light absorbance for the stabilizer not distinguishably different than for the components of the propellant. The illuminating fiber light-exiting end 137 contacts or is in close proximity to a light-contacting portion 153 of the propellant surface 107 and the light penetrates into the propellant surface 107. The light from the illuminating fiber light-exiting end 137 passes through the light-contacting portion 133 and into the propellant surface 107. The light then travels as an internally transmitted beam 145 close beneath the surface 107 of the solid rocket fuel 111. The internally transmitted light beam 145 emerges out of a light-collecting portion 155 of the propellant surface 107 as a transmitted beam to be collected by a collecting fiber light-entering end 139. Both the light-contacting portion 153 and the light-collecting portion 155 are chosen, based not on any unique chemical or physical qualities in comparison to the rest of the surface 107, but rather because of their convenient position for the illuminating fiber light-exiting end 137 to access and shine light on the light-contacting portion 153 and for the collecting fiber light-exiting end. 141 to access the light-collecting portion 155 and collect light emerging from the surface 107 transmitted from the internally transmitted beam 145. The light travels through the collecting fiber 105 to the collecting fiber light-exiting end 141 as the collecting fiber 105 passes into the optical port 101. The light from the collecting fiber light-exiting end 141 is then beamed back through the light directing device 117 (e.g., a lens, a mirror, or an integration sphere). The light from the light directing device 117 is then directed to a UV/visible spectrometer 119 that measures the light intensity of the transmitted light. When the light from the light directing device 117 enters the UV-visible spectrometer 119, the spectrometer shows the light intensity of the transmission light spectra of the stabilizer MNA along with the other components of the M9 nitrate-ester propellant material in the solid rocket fuel 111.

As illustrated in FIGS. 5, 6, and 7, an example of the present application is a method of determining an amount of degradation of stabilizer in solid rocket fuel 111 by measuring either back scattered, reflected or transmitted light given off from the solid rocket fuel 111, the solid rocket fuel 111 including nitrate-ester-based propellant and the stabilizer being either MNA or BTTN. The method includes the following steps. Step a) includes passing light from an illuminating source 115 including light having at least two wavelengths within a spectral range from 100 nm to 200,000 nm wavelengths, a first wavelength or range of wavelengths producing a distinguishably different (i.e. either greater or lesser) light absorbance for the stabilizer than for components of the propellant, and a second wavelength or range of wavelengths producing a light absorbance for the stabilizer not distinguishably different than for the components of the propellant. The light is passed through a light-directing device 117 including a lens and into an illuminating fiber light-entering end 143 and through the illuminating fiber 103. Step b) includes illuminating a light-contacting portion 153 of a surface 107 of the solid rocket fuel 111 with light passing through the illuminating fiber 103 and coming out of the illuminating fiber light-exiting end 137. In the case of back scattered light spectra or transmission light spectra, the illuminating fiber light-exiting end 137 either contacts or comes into close proximity to the light-contacting portion 153 and the illuminating fiber light-exiting end 137 illuminates the light-contacting portion 153 of the surface 107 with light from the illuminating source 115. In the case of reflection light spectra, the illuminating fiber light-exiting end 137 does not contact the surface 107 but rather maintains a slight distance from the surface 107. The to-be-reflected light 159 used to measure reflection light spectra exiting from the illuminating fiber light-exiting end 137 contacts the light-contacting portion 153 of the surface 107. Step c) includes collecting back scattered, reflected or transmitted light being given off from the surface 107 of the solid rocket fuel 111 in response to the illuminating fiber light-exiting end 137 illuminating the light-contacting portion 153 of the surface 107. In the case of back scattered light spectra or transmission light spectra, the collecting of light is by a collecting fiber light-entering end 139 receiving light at the surface 107 of the solid rocket fuel 111 where back scattered or transmitted light is being given off. In the case of reflection light spectra, the collecting fiber light-entering end 139 receives light from a light-collecting device 113 near the surface 107 of the solid rocket fuel 111. The light-collecting device 113 receives reflected light 157 being given off from the light-contacting portion 153 of the surface 107. The light-collecting device 113 includes a device selected from the group consisting of a lens, a mirror, and an integration sphere. Step d) includes passing collected back scattered, reflection or transmission light through the collecting fiber 105 and out the collecting fiber light-exiting end 141 through the light-directing device 117 and into a spectrometer 119. Step e) includes determining with the spectrometer 119 the light intensities of the first light wavelength and the second light wavelength of the back scattered, reflected or transmitted light being given off from the surface 107 of the solid rocket fuel 111.

In yet another embodiment of the method for measuring the back scattered, reflection or transmission light spectra illustrated in FIGS. 5, 6 and 7, the nitrate-ester-based propellant is a double base NC/NG propellant comprised of nitrocellulose, nitroglycerin, and $KNO_3$. In another embodiment, the nitrate-ester-based propellant further includes carbon black.

In still another embodiment of the method for measuring the back scattered, reflection or transmission light spectra illustrated in FIGS. 5, 6, and 7, the stabilizer is MNA and the first wavelength or range of wavelengths is from a blue light having at least one wavelength in a range from 450 to 490 nm and the second wavelength or range of wavelengths is from a green light having at least one wavelength in a range from 501 to 543 nm. In a further embodiment, the first light wavelength includes 473 nm and the second light wavelength includes 532 nm.

In an embodiment of the method for measuring the back scattered light spectra, illustrated in FIG. 5, in the illuminating step, when the illuminating fiber light-exiting end 137 contacts or is in close proximity to and delivers light to the light-contacting portion 153 of the surface 107 of the solid rocket fuel 111, the light penetrates into and-forms back scattered light 109 beneath the surface 107 of the solid rocket fuel 111. The back-scattered light 109 exits the solid rocket fuel 111 at the light-collecting portion 155 of the surface 107 of the solid rocket fuel 111. Furthermore, in the collecting step, the collecting fiber light-entering end 139 contacts or is in close proximity to the light-collecting portion 155 of the surface 107 of the solid rocket fuel 111 and collects back scattered light-exiting the light-collecting portion 155.

In another embodiment of the method based on measuring the back scattered light spectra illustrated in FIG. 5, at the surface 107 of the solid rocket fuel 111, the light-contacting portion 153 of the surface 107 and the light-collecting portion 155 of the surface 107 are at a distance less than 1 mm apart. The collecting fiber light-entering end 139 and the illuminating fiber light-exiting end 137 are substantially parallel to each other in an area proximate to the light-contacting portion 153 and light-collecting portions 155 of the surface 107 of the solid rocket fuel.

In an embodiment of the method for measuring the reflection light spectra illustrated in FIG. 6, in the illuminating step, when the illuminating fiber light-exiting end 137 delivers to-be-reflected light 159 to the light-contacting portion 153 of the surface 107 of the solid rocket fuel 111, the illuminating fiber light-exiting end 137 does not contact the light-contacting portion 153 of the surface 107 but is in close proximity to the light-contacting portion 153. The to-be-reflected light 159 is reflected back off the light-contacting portion 153 of the surface 107 as reflected light 157. In the collecting step, when the to-be-reflected light 159 is reflected back off the light-contacting portion 153 of the surface 107 of the solid rocket fuel 111 as reflected light 157, the light-collecting device 117, not contacting the light-contacting portion 153 but in close proximity to the light-contacting portion 153, collects the reflected light 157 from the light-contacting portion 153 of the surface 107 of the solid rocket fuel 111. The reflected light 157 from the light-contacting portion 153 hits the light-collecting device 117 at more than one angle. Furthermore, the light-collecting device 117 directs the collected light to the collecting fiber light-entering end 139, so that the light directed from the light-collecting device 117 enters the collecting fiber light-entering end 139.

In an embodiment of the method for measuring the transmission light spectra illustrated in FIG. 7, in the illuminating step, when the illuminating fiber light-exiting end 137 contacts or is in close proximity to and delivers light to the light-contacting portion 153 of the surface 107 of the solid rocket fuel 111, the light penetrates the surface 107. The light then travels and is transmitted as an internally transmitted beam 145 close beneath the surface of the solid rocket fuel 111 from the light-contacting portion 153 to the light-collecting portion 155. The internally transmitted light beam 145 emerges out of a light-collecting portion 155 of the propellant surface 107. The collecting fiber light-entering end 139 contacts or is in close proximity to the light-collecting portion 155 of the surface 107 of the solid rocket fuel 111 and collects light transmitted from the surface 107 at the light-collecting portion 155.

Another embodiment, illustrated in FIGS. 5, 6, and 7, is a spectrometric system that measures light intensity of back scattered, reflected or transmitted light. The spectrometric system includes: a solid rocket fuel 111 surrounded by a metal shell 123, the solid rocket fuel 111 including a nitrate-ester-based propellant and a stabilizer selected from either MNA stabilizer or BTTN stabilizer. The spectrometric system also includes: a) a spectrometer 119 to determine the light intensities of back scattered, reflected or transmitted light; b) an illuminating source 115 giving off light including at least two light wavelengths within a spectral range from 100 nm to 200,000 nm wavelength, a first wavelength or range of wavelengths producing a distinguishably different light absorbance for the stabilizer than for the propellant components, and a second wavelength or range of wavelengths producing a light absorbance for the stabilizer not distinguishably different than for the propellant components; and c) a light-directing device 117 including a lens through which light passes in a first direction toward the solid rocket fuel 111 and in an opposite direction toward the spectrometer 119. The spectrometric system also includes an illuminating fiber 103 including a) an illuminating fiber light-entering end 143 to collect light coming from the illuminating source 115 through the light-directing device 117; b) the illuminating fiber 103 itself through which the light travels; and c) an illuminating fiber light-exiting end 137 to illuminate a light-contacting portion 153 of a surface 107 of a solid rocket fuel 111 by either contacting the light-contacting portion 153 or being in close proximity to the light-contacting portion 153. The spectrometric system also includes a collecting fiber 105 including a) a collecting fiber light-entering end 139 to collect back scattered, reflected or transmitted light being given off from the surface 107 of the solid rocket fuel 111 or from a light-collecting device 113 near the surface of the solid rocket fuel 111; b) the collecting fiber 105 itself through which the light travels; and c) a collecting fiber light-exiting end 141 to deliver light to and through the light-directing device 117 and toward the spectrometer 119. In the spectrometric system, the light-collecting device 113 receives reflected light being given off from the light-contacting portion 153 of the surface 107. The light-collecting device including a device selected from the group consisting of a lens, a mirror and an integration sphere.

In yet another embodiment of the system for measuring back scattered, reflected or transmitted light illustrated in FIGS. 5, 6 and 7, the nitrate-ester-based propellant is a double base NC/NG propellant comprised of nitrocellulose, nitroglycerin, and $KNO_3$. In another embodiment, the nitrate-ester-based propellant further includes carbon black. In still another embodiment of the system, the stabilizer is MNA and the first wavelength is from a blue light having at least one wavelength in a range from 450 to 490 nm and the second wavelength is from a green light having at least one wavelength in a range from 501 to 543 nm. In a further embodiment, the first light wavelength is 473 nm wavelength and the second light wavelength is 532 nm wavelength.

In another embodiment of the system for measuring back scattered, reflected or transmitted light to determine light intensity as illustrated in FIGS. 5, 6 and 7, the system further includes an optical port 101 in the metal shell 123. The optical port 101 is positioned between the light-directing device 117 and the surface of the solid rocket fuel 111. The optical port 101 includes an opening in the metal shell 123 through which the illuminating fiber 103 and the collecting fiber 105 pass into a space 151 between the metal shell 123 and the surface 107 of the solid rocket fuel 111 to give the illuminating fiber light-exiting end 137 and the collecting fiber light-entering end 139 contact or close proximity with the surface 107 of the solid rocket fuel 111.

In another embodiment of the system for measuring back scattered, reflected or transmitted light to determine light intensity as illustrated in FIG. 5, the illuminating fiber light-exiting end 137 contacts or is in close proximity to the light-contacting portion 153 of the surface 107 of the solid rocket fuel 111 and the collecting fiber light-entering end 139 contacts or is in close proximity to a light-collecting portion 155 of the surface 107 of the solid rocket fuel 111. Furthermore, the light-contacting portion 153 and the light-collecting portion 155 are at a sufficient distance from each other to allow light from the illuminating fiber light-exiting end 137 to penetrate the surface 107 at the light-contacting portion 153 and form back scattered light 109 inside the solid rocket fuel 111 between the light-contacting portion 153 and the light-collecting portion 155. Additionally, the back scattered light 109 emerges from the light-collecting portion 155 of the solid rocket fuel 111. The emerging light travels to the collecting fiber light-entering end 139.

In another embodiment of the system for measuring back scattered light to determine the light intensity illustrated in FIG. 5, the light-contacting portion 153 and the light-collecting portion 155 are less than 1 mm apart on the surface 107 of the solid rocket fuel 111. Furthermore, the illuminating fiber light-exiting end 137 and the collecting fiber light-entering end 139 are substantially parallel to each other in an area proximate to the light-contacting portion 153 and light-collecting portion 155 of the surface 107 of the solid rocket fuel 111. In another embodiment of the system illustrated in FIG. 5, the light-contacting portion 153 and the light-collecting portion 155 are at most 200 microns apart from each other.

In another embodiment of the system for measuring reflection light to determine the light intensity as illustrated in FIG. 6, the illuminating fiber light-exiting and 137 does not contact the light-contacting portion 153 of the surface 107 but is in close proximity to the light-contacting portion 153 of the solid rocket fuel 111. The light-collecting device 113 also not contacting but in close proximity to the light-contacting portion 153 of the surface 107 light-collecting collects reflected light 157 from the light-contacting portion 153 of the surface 107 of the solid rocket fuel 111. The reflected light 157 travels from the light-contacting portion 153 and enters the light-collecting device 113 at more than one angle. In addition, the collecting fiber light-entering end 139 is positioned with respect to the light-collecting device 113, so that the reflected light 157 collected in the light-collecting device 113 is directed to the collecting fiber light-entering end 139.

In yet another embodiment of the system illustrated in FIG. 7, the illuminating fiber light-exiting end 137 contacts or is in close proximity to the light-contacting portion 153 of the surface 107 of the solid rocket fuel 111. The collecting fiber light-entering end 139 contacts or is in close proximity to the light-collecting portion 155 of the surface 107 of the solid rocket fuel 111. The light is directed from the illuminating fiber light exiting end 137 to the light-contacting portion 153 of the surface 107. The light then travels as an internally transmitted beam 145 from the light-contacting portion 153 close beneath the surface 107 of the solid rocket fuel 111. The internally transmitted beam 145 emerges out of a light-collecting portion 155 of the propellant surface 107. The internally transmitted beam 145 emerges from the light-collecting portion 155 of the surface 107 and enters the collecting fiber light-entering end 139.

To verify these proposed measuring methods and configurations, the following experiments were conducted and described in the Examples below.

EXAMPLES

Example 1

Figure 8:
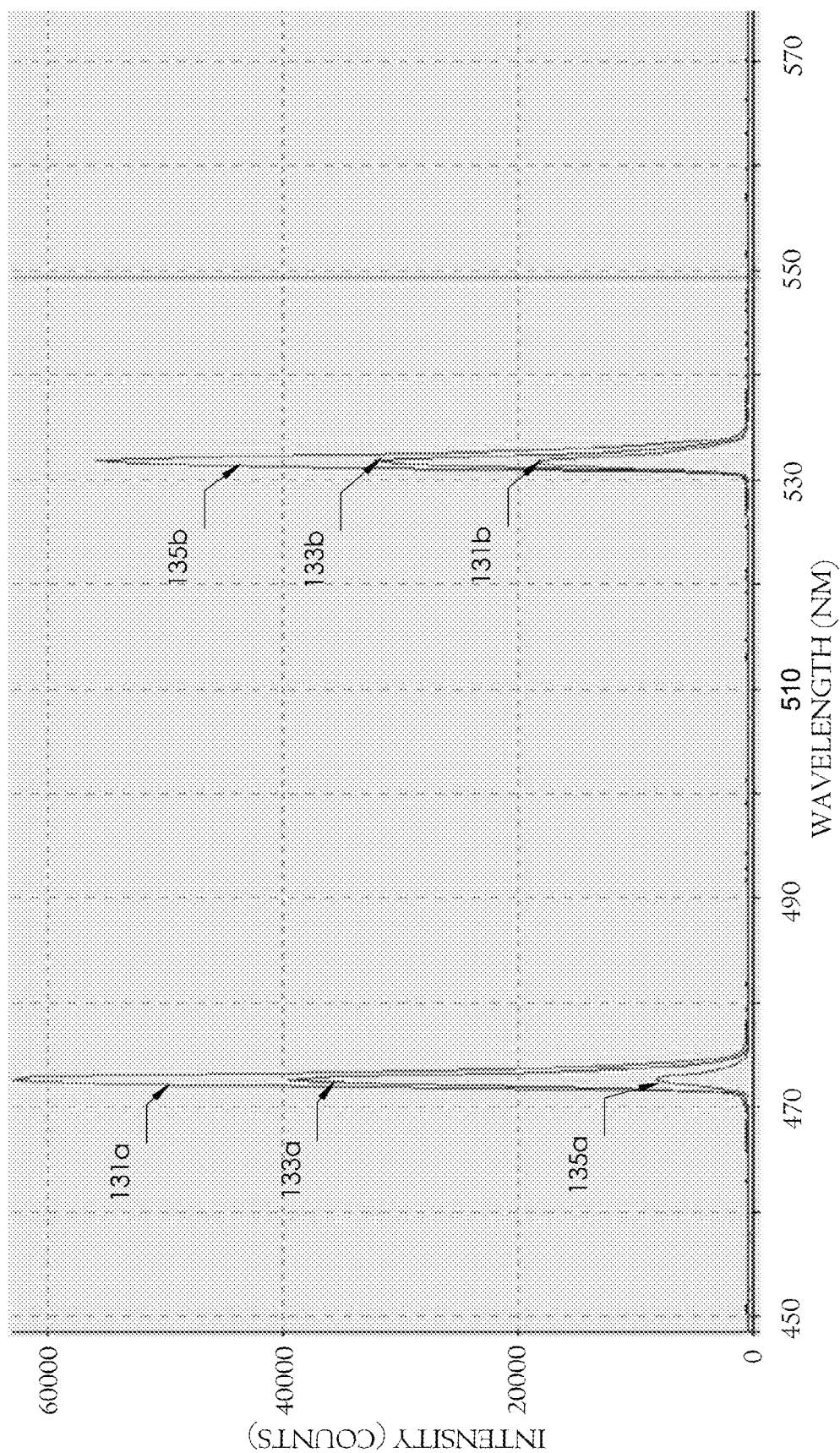
FIG. 8 has plots of wavelength vs. intensity of the experimentally measured, back scattered light spectra of three samples of M9 nitrate-ester propellant including MNA.

Three samples were used to measure light intensity in blue and green light of MNA and its accompanying M9 nitrate-ester propellant. An Ocean Optics 2000® UV/visible spectrometer was used to measure the spectra generated from the light of the illuminating fiber 103 having passed through the samples and having emerged as back scattered light which is subsequently collected in a collecting fiber 105. FIG. 8 was plotted to show three different MNA concentration levels across the visible spectra for the three samples: the first sample containing 0 wt % MNA in M9 nitrate-ester propellant, the second sample containing 0.45 wt % MNA in M9 nitrate-ester propellant, and the third sample containing 0.7 wt % MNA in M9 nitrate-ester propellant. All three samples were without carbon black. In FIG. 8, the back scattered light spectra for the first sample showed two peaks: the blue peak 131A and the green peak 131b. Also in FIG. 8, the back scattered light spectra for the second sample showed two peaks: the blue peak 133a and the green peak 133b. Finally, in FIG. 8, the back scattered light spectra for the third sample showed two peaks: the blue peak 135a and the green peak 135b. It was clearly shown in this example that there was a dramatic change, based on the presence of MNA, in the ratio of signal intensities obtained for the three samples with blue light (473 nm) vs. green light (532 nm). FIG. 8 showed that the signal intensity at the blue light wavelength is strongest at 473 nm when there is no MNA. FIG. 8 also shows that the signal intensity at the blue light wavelength decreases as the concentration level of MNA increases. This is due to the heavy absorption of MNA at the UV/blue spectral region which thus decreases the signal intensity in the UV/blue spectral region.

Example 2

Figure 9:
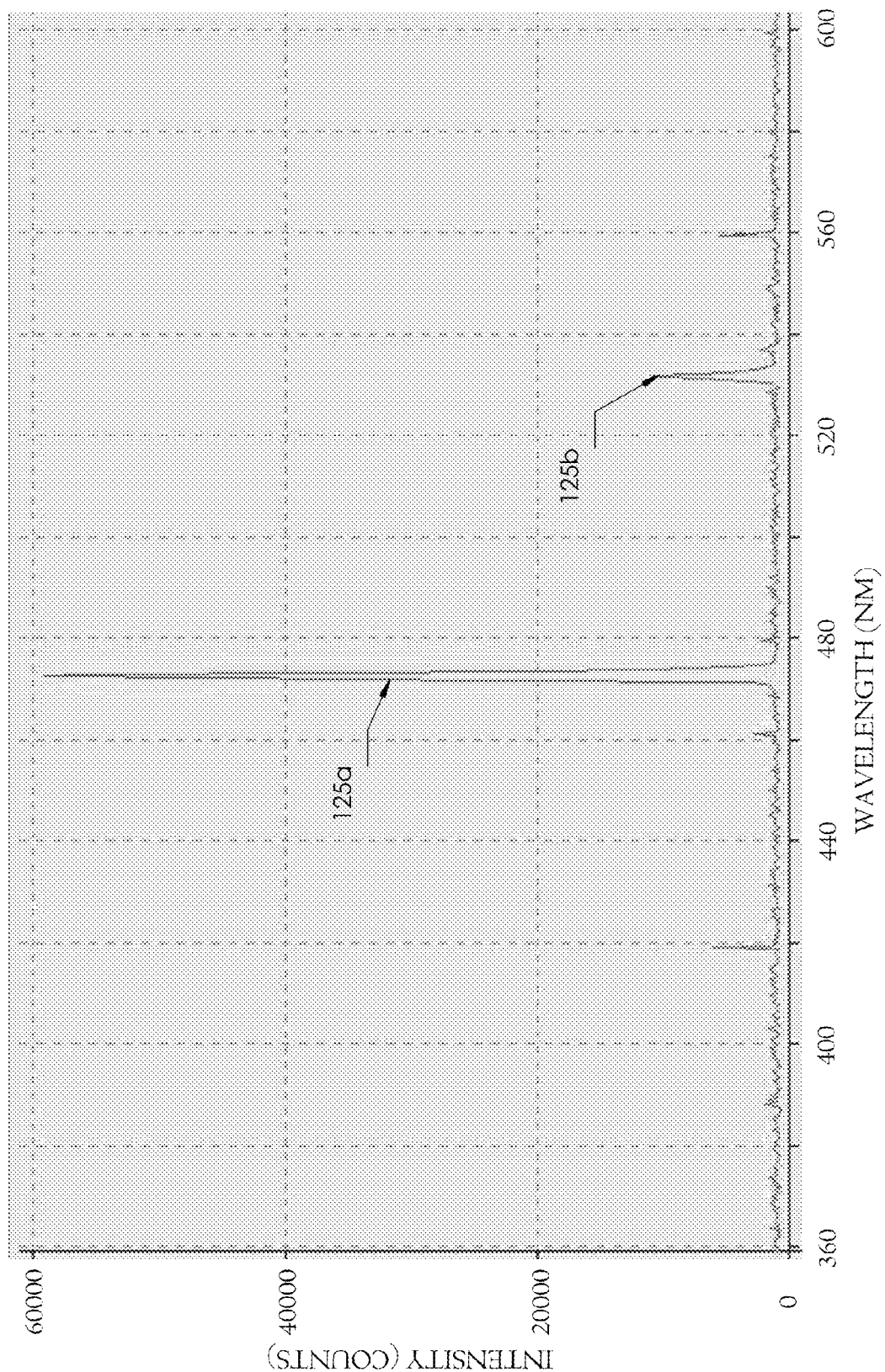
FIGS. 9, 10 and 11 have plots of wavelength vs. intensity of the experimentally measured, back scattered light spectra of MNA in an M9 nitrate-ester propellant including MNA.
Figure 10:
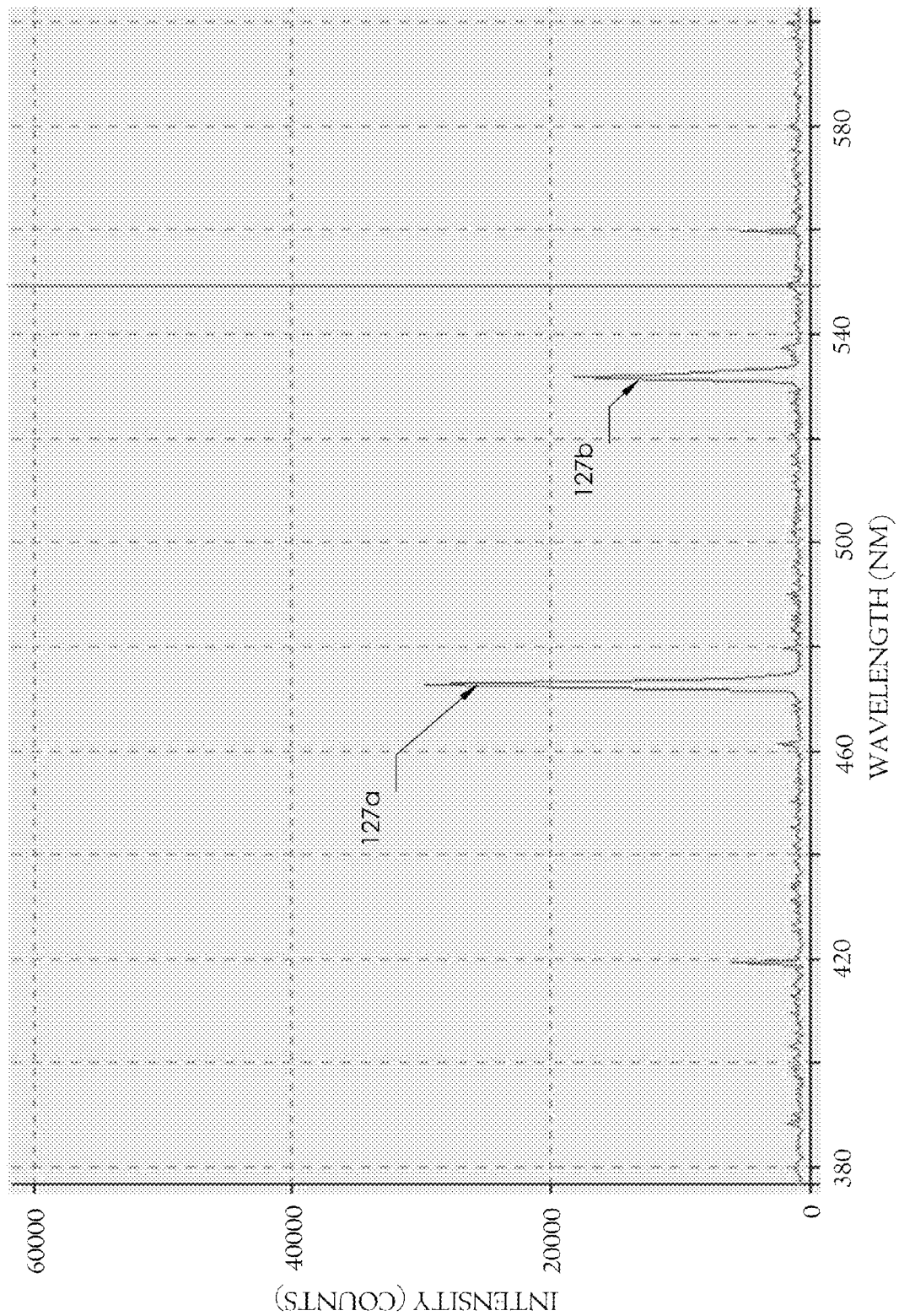
Figure 11:
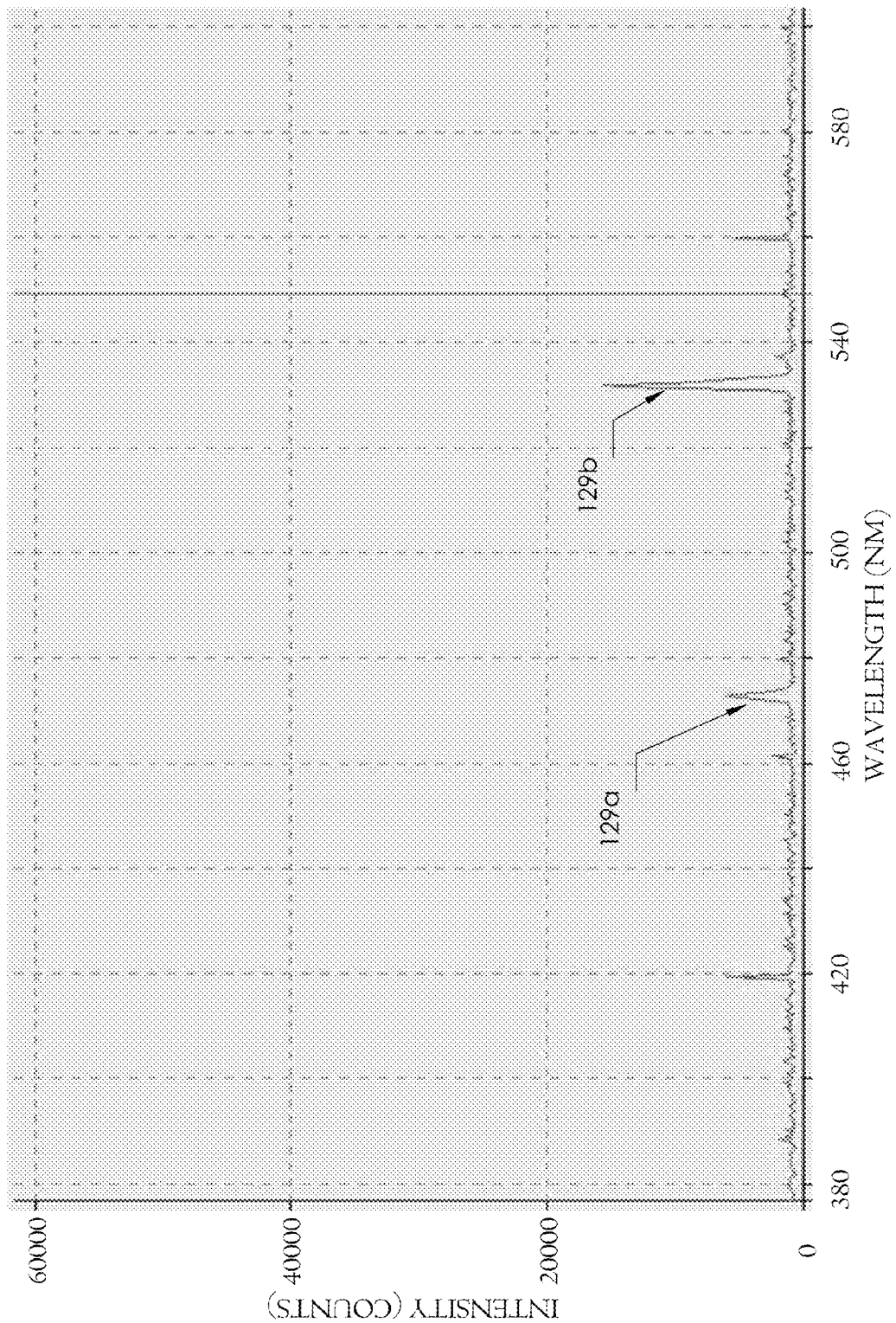

1 wt % carbon black was added to three samples having the same compositions as the three previously described first, second and third samples of Example 1, the back scattered light spectra of which are shown in FIG. 8. The first sample had a concentration level of 0 wt % MNA in M9 nitrate-ester propellant. The second sample had a concentration level of 0.45 wt % MNA in M9 nitrate-ester propellant. The third sample had concentration level of 0.7 wt % MNA in M9 nitrate-ester propellant. 1 wt % carbon black was added to the samples to simulate actual M9 nitrate-ester propellant components used in missile systems. An Ocean Optics 2000® UV/visible spectrometer 119 was used to measure the back scattered light spectra generated from the light of the illuminating fiber 103 having passed through the samples and emerging as back scattered light which is subsequently collected in a collecting fiber 105 and ultimately passed to the spectrometer 119. FIGS. 9, 10 and 11 showed the experimentally measured back scattered light spectra of the varying concentrations of MNA in M9 nitrate-ester propellant.

FIG. 9 showed the back scattered light spectra of the first sample, which had 0 wt % stabilizer MNA in M9 nitrate-ester propellant with 1 wt % carbon black. In FIG. 9, the signal intensity counts shown by the blue peak 125a and the green peak 125b were respectively 59768 (at 472.59 nm) and 11690 (at 531.91 nm). The Peak Ratio of blue to green signal intensities was 5.11.

FIG. 10 showed the back scattered light spectra of the second sample which had 0.45 wt % MNA in M9 nitrate-ester propellant with 1 wt % carbon black. In FIG. 10, the blue peak 127a and the green peak 127b signal intensities were respectively 29507 (at 472.59 nm) and 18168 (at 531.91 nm). The Peak Ratio of blue to green signal intensities was 1.62.

FIG. 11 showed the back scattered light spectra of the third sample which had 0.7 wt % MNA in M9 nitrate-ester propellant with 1 wt % carbon black. In FIG. 11, the blue peak 129a and the green peak 129b signal intensity counts were respectively 5357 (at 472.59 nm) and 15323 (at 531.91 nm). The Peak Ratio of blue to green signal intensities was 0.35.

Again, it was clearly seen that there was a marked difference among the three samples between the ratios of signal intensity counts for blue light (473 nm) vs. green light (532 nm). The signal intensity count of blue light decreased as the concentration level of MNA increased due to the heavy absorption of MNA in the blue spectral region. In contrast, the signal intensity count of green light was not markedly changed because there was not increased MNA absorption in the green spectral region, unlike the blue spectral region. Thus the concentration level of MNA in the three samples was measured and compared, with carbon black present, by measuring light intensity in both the blue and green spectral regions.

Example 3

To validate the feasibility of the system using the reflection light spectra, the following proof-of-concept experiment was conducted. Three M9 nitrate-ester propellant samples with MNA as stabilizer were obtained from the outer surface layer 107 of a solid rocket fuel 111. The first sample was the original M9 nitrate-ester propellant. The second sample was acceleratively aged at around 71° C. for 28 days. The third sample was acceleratively aged at around 71° C. for 43 days. Under these accelerated aging conditions, the first and second samples had similar concentration levels of MNA (around 0.5 wt %) and the third one had a concentration level of MNA about half of the levels of the first and second samples (around 0.25 wt %).

Figure 12:
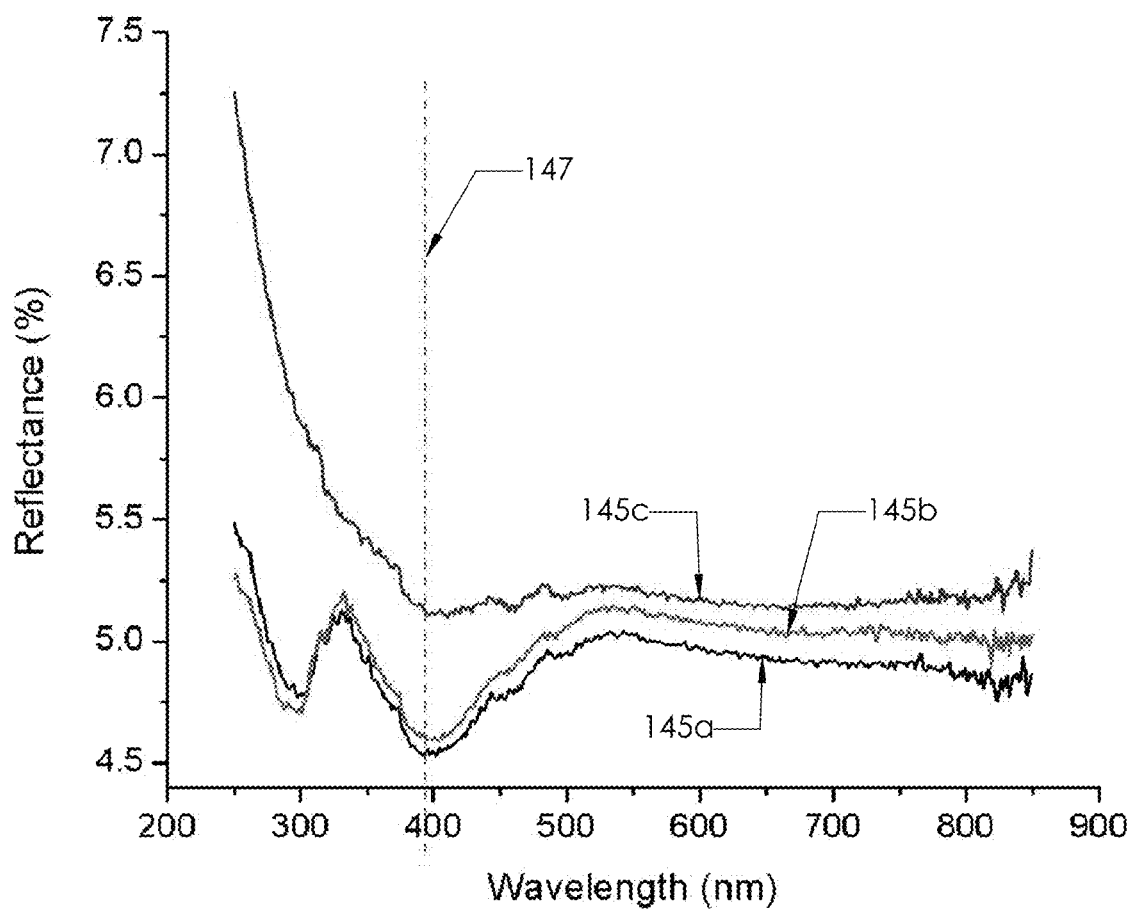
FIG. 12 has plots of wavelength vs. percent reflectance of the experimentally measured reflection light spectra of three cut, outer-surface layer samples of M9 nitrate-ester propellant including MNA.

FIG. 12 showed the experimentally measured reflection light spectra. An Ocean Optics 2000® UV/visible spectrometer 119 was used to measure the spectra generated from the light of the illuminating fiber 103 having passed through the samples and emerging as reflection light 157 which is subsequently collected in a collecting fiber 105 and ultimately passed to the spectrometer 119. It clearly showed that the reflection light spectra for the first sample 145a and the reflection light spectra for the second sample 145b had similar patterns obtained from reflection light spectroscopy. However, the third sample 145c had a higher reflection light spectra at around 400 nm due to the reduced absorption from MNA at that spectral region. This was because of reduced presence of MNA as a result of the extreme aging conditions. A vertical line 147 indicated the area around 400 nm wavelength on the graph (approximately the blue spectral region). These experimental results confirmed that the proposed reflection configuration worked by detecting the presence of MNA.

Example 4

Figure 13:
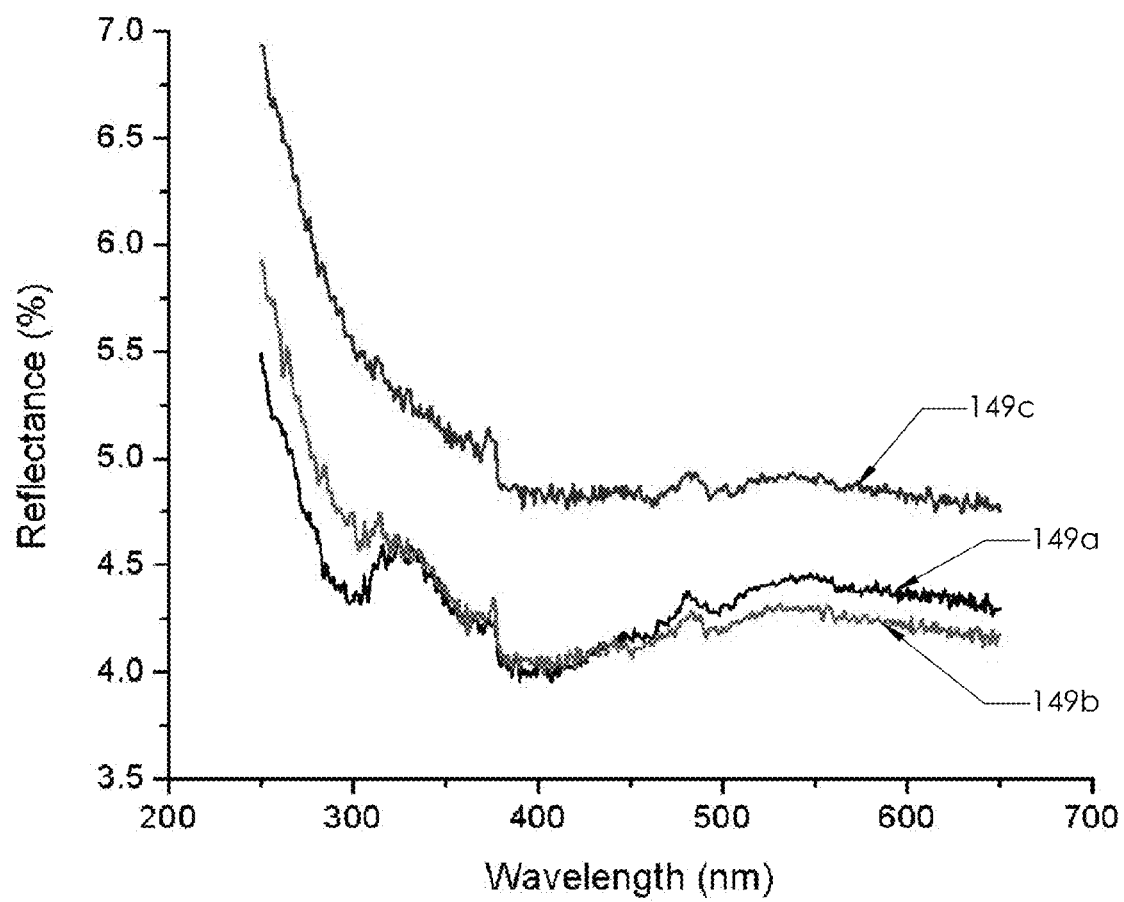
FIG. 13 has plots of wavelength vs. percent reflectance of the experimentally measured reflection light spectra of three cut, underneath-the-surface layer samples of M9 nitrate-ester propellant including MNA.

To ensure that the proposed detection method for reflection light was effective not only for the surface layer of the solid rocket fuel 111 but also for beneath the surface layer of the solid rocket fuel 111, the following experiment was conducted. The first, second and third samples were cut from underneath the outer surface 107 of a solid rocket fuel 111. An Ocean Optics 2000® UV/visible spectrometer 119 was used to measure the reflection light spectra generated from the light of the illuminating fiber 103 having passed through the samples and emerging as reflected light 157 which is subsequently collected in a collecting fiber 105 and ultimately passed to the spectrometer 119. Also, as in Example 3, the first sample was the original M9 nitrate-ester propellant; the second sample was acceleratively aged at around 71° C. for 28 days; and the third sample was acceleratively aged at around 71° C. for 43 days. As shown in FIG. 13, the reflection light spectra for the first sample 149a and the reflection light spectra for the second sample 149b indicated similar concentration levels of MNA, (around 0.5 wt %). However, the reflection light spectra for the third sample 149c indicated a concentration level of MNA about half of the level of the first and second samples (around 0.25 wt %). FIG. 13 thus showed the experimentally measured reflection light spectra for the beneath-the-surface-layer propellant samples. Again, as in Example 3, one was able to clearly differentiate the third sample from the first and second samples due to the different concentration levels of MNA. This was due to the reduced absorption from MNA (at around 400 nm wavelength, at approximately the blue spectral region), as shown in FIG. 13) because of a reduced presence of MNA as a result of the extreme aging conditions. Thus, based on Examples 3 and 4, the proposed reflection light spectra method worked to determine MNA concentration in M9 for both the outer surface layer propellant and the beneath-the-surface layer propellant.

Example 5

Figure 14:
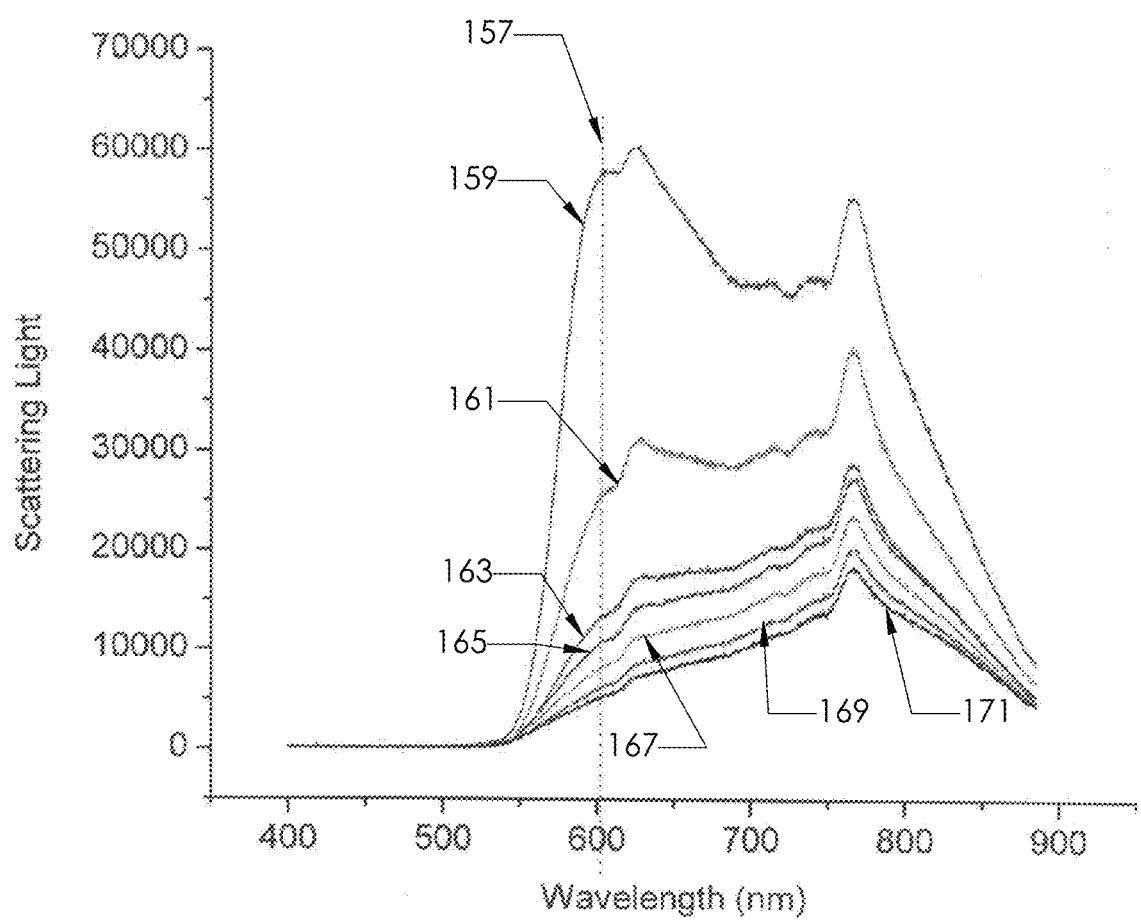
FIG. 14 has plots of wavelength vs. scattering light of the experimentally measured back scattered light spectra of seven cut samples of MK90 nitrate-ester propellant including 1,2,4-butane triol trinitrate (BUN) as a stabilizer.

Nosih-AA@ (MK90) minimum smoke double base nitrate-ester propellant samples with initial amounts of 2 weight % BUN as stabilizer were measured by the back scattered light spectroscopic system, as illustrated in FIG. 4. The samples 159, 161, 163, 165, 167, 169 and 171 were provided by the manufacturer and were acceleratively aged for different time periods (from 0 to 6 weeks at 75° C.). Aging at 75° C. for 6 weeks was equivalent to a 25 year aging period at normal storage conditions (approximating the normal life time of the propellant). The experimentally measured back scattered light spectra for the samples were shown on FIG. 14. An Ocean Optics 2000® UV/visible spectrometer 119 was used to measure the back scattered light spectra generated from the light of the illuminating fiber 103 having passed through the samples and emerging as back scattered light which is subsequently collected in a collecting fiber 105 and ultimately passed to the spectrometer 119. FIG. 14 showed the following spectra: 159, a 0 week aged sample; 161, a 1 week aged sample; 163, a 2 week aged sample; 165, a 3 week aged sample; 167, a 4 week aged sample; 169, a 5 week aged sample; and 171, a 6 week aged sample. During the course of accelerative aging of the samples, the amount of measurable BTTN decreased to a low of approximately 0.5 weight percent. A dashed vertical line 157 indicated the area around 603 nm wavelength on the graph which is approximately where the back scattered light peak occurs for the BUN stabilizer/MK90 propellant composition. A reference peak of around 790 nm can also be seen on FIG. 14 as a second smaller peak to the right of the first peak. The increased absorption over time was due to the change in chemical structure of the BTTN stabilizer/MK90 propellant composition during the aging process. The newer the BUN stabilizer/MK90 propellant composition, the less absorption occurred at around 603 nm wavelength, thus the higher light intensity/lesser absorption in the first sample and decreasing light intensity/higher absorption in the subsequent aging samples. By the same token, the newer the BUN stabilizer/MK90 propellant composition, the smaller the scattering light intensity ratio between the 603 nm peak and the 790 nm reference peak. Thus in this case, light absorption increases as BTTN decreases in the MK90 propellant composition.

While several embodiments have been described in detail, it will be apparent to those skilled in the art that the disclosed embodiments may be modified. Therefore, the foregoing description is to be considered exemplary rather than limiting.

What is claimed is:

1. A method of determining an amount of degradation of stabilizer in a solid state rocket fuel by measuring intensity of either back scattered, reflected or transmitted light in the solid state rocket fuel, the method comprising the steps of:
   providing the solid state rocket fuel, the solid state rocket fuel being either 1) a double-base NC/NG solid state propellant fuel (M9) with a 2-methyl-4-nitroaniline stabilizer (MNA), or 2 Nosih-AA2 minimum smoke double base solid state propellant fuel (MK90) with a 1,2,4-butanetriol trinitrate stabilizer (BTTN);
   passing light having a spectral range from 100 nm to 200,000 nm from an illuminating source, the light including 1) a first wavelength or range of wavelengths producing a distinguishably greater or lesser light absorbance for the stabilizer than for components of the solid state rocket fuel, and 2) a second wavelength or range of wavelengths producing a light absorbance for the stabilizer not distinguishably different than for the components of the solid state rocket fuel, the light having passed through a light-directing device including a lens and into an illuminating fiber light-entering end and through the illuminating fiber;
   illuminating a light-contacting portion of a surface of the solid state rocket fuel with light coming out of the illuminating fiber light-exiting end, and the illuminating fiber light-exiting end either contacting or coming into close proximity to the light-contacting portion, the illuminating fiber light-exiting end illuminating the light-contacting portion of the surface with the light from the illuminating source;
   collecting backscattered, reflected or transmitted light being given off from the surface of the solid state rocket fuel in response to the illuminating fiber light-exiting end illuminating the light-contacting portion of the surface, wherein the collecting of light is by a collecting fiber light-entering end either contacting or coming into close proximity to the surface of the solid state rocket fuel where back scattered or transmitted light is being given off; or the collecting fiber light-entering end gathering light from a light-collecting device near the surface of the solid state rocket fuel, the light-collecting device receiving reflected light being given off from the light-contacting portion of the surface, wherein the light-collecting device includes a device selected from the group consisting of a lens, a mirror and an integration sphere;
   passing light through the collecting fiber and out a collecting fiber light-exiting end through the light-directing device and into a spectrometer; and
   determining with the spectrometer the light intensities of the back scattered, reflected or transmitted light being given off from the surface of the solid state rocket fuel.

2. The method according to claim 1, wherein the double-base NC/NG solid state propellant fuel (M9) is comprised of nitrocellulose, nitroglycerin and $KNO_3$.

3. The method according to claim 2, wherein the double-base NC/NG solid state propellant fuel (M9) further comprises carbon black.

4. The method according to claim 1, wherein, when the stabilizer is MNA, the first wavelength or range of wavelengths is from a blue light having at least one wavelength in a range from 450 to 490 nm, and the second wavelength or range of wavelengths is from a green light having at least one wavelength in a range from 501 to 543 nm.

5. The method according to claim 4, wherein the first wavelength is 473 nm and the second wavelength is 532 nm.

6. The method according to claim 1, wherein, in the illuminating step, when the illuminating fiber light-exiting end contacts or is in close proximity to the surface of the solid state rocket fuel and delivers light to the light-contacting portion, the light penetrates into and forms back scattered light beneath the surface of the solid state rocket fuel and the back scattered light exits the solid state rocket fuel at a light-collecting portion of the surface of the solid state rocket fuel; and wherein, in the collecting step, the collecting fiber light-entering end contacts or is in close proximity to the light-collecting portion of the surface of the solid state rocket fuel and collects back scattered light exiting the light-collecting portion.

7. The method according to claim 6, wherein, at the surface of the solid state rocket fuel, the light-contacting portion of the surface and the light-collecting portion of the surface are at a distance less than 1 mm apart, and the illuminating fiber light-entering end and the collecting fiber light-exiting end are substantially parallel to each other in an area proximate to the light-contacting and light-collecting portions of the surface of the solid state rocket fuel.

8. The method according to claim 1, wherein, in the illuminating step, when the illuminating fiber light-exiting end delivers to-be-reflected light to the light-contacting portion of the surface of the solid state rocket fuel, the illuminating fiber light-exiting end does not contact the light-contacting portion of the surface but is in close proximity to the light-contacting portion, the to-be-reflected light being reflected back off the light-contacting portion of the surface;

wherein, in the collecting step, when the light is reflected back off the light-contacting portion of the surface of the solid state rocket fuel, the light-collecting device, not contacting the light-contacting portion but in close proximity to the light-contacting portion, collects the reflected light from the light-contacting portion of the surface of the solid state rocket fuel, the reflected light from the light-contacting portion hitting the light-collecting device at more than one angle;

and wherein, the light-collecting device directs light to the collecting fiber light-entering end, so that the light directed from the light-collecting device enters the collecting fiber light-entering end.

9. The method according to claim 1, wherein, in the illuminating step, when the illuminating fiber light-exiting end contacts or is in close proximity to the light-contacting portion of the surface of the solid state rocket fuel and delivers light to the light-contacting portion, the light penetrates the surface, becoming an internally transmitted beam close beneath the surface of the solid state rocket fuel from the light-contacting portion to a light-collecting portion of the surface;

and wherein, in the collecting step, the collecting fiber light-entering end contacts or is in close proximity to the light-collecting portion of the surface of the solid state rocket fuel and collects light from the internally transmitted beam transmitted from the surface at the light-collecting portion.

10. A spectrometric system that measures intensity of back scattered, reflected or transmitted light to determine an amount of degradation of stabilizer in a solid state rocket fuel, comprising:
the solid state rocket fuel surrounded by a metal shell, the solid state rocket fuel being
either 1) a double-base NC/NG solid state propellant fuel (M9) with a 2-methyl-4-nitroaniline stabilizer (MNA), or 2) a Nosih-AA2 minimum smoke double base solid state rose fuel (MK90 and with a 1,2,4-butanetriol trinitrate stabilizer (BTTN);
a spectrometer to determine the light intensities of the back scattered, reflected or transmitted light;
an illuminating source giving off light having a spectral range from 100 nm to 200,000 nm wavelengths including 1)a first wavelength or range of wavelengths producing a distinguishably greater or lesser light absorbance for the stabilizer than for components of the solid state rocket fuel, and 2)a second wavelength or range of wavelengths producing a light absorbance for the stabilizer not distinguishably different than for the components of the solid state rocket fuel;
a light-directing device including a lens through which light passes in a first direction toward the solid state rocket fuel and in an opposite direction toward the spectrometer;
an illuminating fiber including a) an illuminating fiber light-entering end to collect light coming from the illuminating source through the light-directing device; b) the illuminating fiber itself through which the light travels; and c) an illuminating fiber light-exiting end to illuminate a light-contacting portion of a surface of the solid state rocket fuel by either contacting or being in close proximity to the light-contacting portion;
and a collecting fiber including a) a collecting fiber light-entering end to collect back scattered, reflected or transmitted light being given off from the surface of the solid state rocket fuel or from a light-collecting device near the surface of the solid state rocket fuel; b) the collecting fiber itself through which the light travels; and c) a collecting fiber light-exiting end to deliver light to and through the light-directing device and toward the spectrometer;
wherein the light-collecting device receives reflected light being given off from the contacting portion of the surface, the light-collecting device including a device selected from the group consisting of a lens, a mirror and an integration sphere.

11. The system according to claim 10, wherein the double-base NC/NG solid state propellant fuel (M9) is comprised of nitrocellulose, nitroglycerin and KNO3.

12. The system according to claim 11, wherein the double-base NC/NG solid state propellant fuel (M9) further comprises carbon black.

13. The system according to claim 10, wherein, when the stabilizer is MNA, the first wavelength or range of wavelengths is from a blue light having at least one wavelength in a range from 450 to 490 nm and the second wavelength or range of wavelengths is from a green light having at least one wavelength in a range from 501 to 543 nm.

14. The system according to claim 13, wherein the first light wavelength is 473 nm and the second light wavelength is 532 nm.

15. The system according to claim 10, further comprising an optical port in the metal shell, the optical port being positioned between the light-directing device and the surface of the solid state rocket fuel, the optical port including an opening in the metal shell through which the illuminating fiber and the collecting fiber pass into a space between the metal shell and the surface of the solid state rocket fuel to give the illuminating fiber light-exiting end and the collecting fiber light-entering end contact or close proximity with the surface of the solid state rocket fuel.

16. The system according to claim 10, wherein the illuminating fiber light-exiting end contacts or is in close proximity to the light-contacting portion of the surface of the solid state rocket fuel and the collecting fiber light-entering end contacts or is in close proximity to a light-collecting portion of the surface of the solid state rocket fuel;

and wherein the light-contacting portion and the light-collecting portion are at a sufficient distance from each other to allow light from the illuminating fiber light-exiting end to penetrate the surface at the light-contacting portion and form back scattered light inside the state solid rocket fuel between the light-contacting portion and the light-collecting portion, the back scattered light emerging from the light-collecting portion to the collecting fiber light-entering end.

17. The system according to claim 16, wherein the light-contacting portion and the light-collecting portion are less than 1 mm apart on the surface of the solid state rocket fuel;

and wherein the illuminating fiber light-exiting end and the collecting fiber light-entering end are substantially parallel to each other in an area proximate to the light-contacting portion and the light-collecting portion of that surface of the solid state rocket fuel.

18. The system according to claim 17, wherein the light-contacting portion and the light-collecting portion are at most 200 microns apart from each other.

19. The system according to claim 10, wherein the illuminating fiber light-exiting end is in close proximity but does not contact the light-contacting portion of the surface of the solid state rocket fuel, and the light-collecting device also is in close proximity to but does not contact the light-contacting portion; wherein the light-collecting device collects reflected light from the light-contacting portion of the surface of the solid state rocket fuel, the reflected light travelling from the light-contacting portion and entering the light-collecting device at more than one angle;

and wherein the collecting fiber light-entering end is positioned with respect to the light-collecting device, so that the reflected light collected in the light-collecting device is directed to the collecting fiber light-entering end.

20. The system according to claim 10, wherein the illuminating fiber light-exiting end contacts or is in close proximity to the light-contacting portion of the surface of the solid state rocket fuel, and the collecting fiber light-entering end contacts or is in close proximity to the light-collecting portion of the surface of the solid state rocket fuel; wherein the light is directed to the light-contacting portion of the surface from the illuminating fiber light exiting end and the light becomes an internally transmitted beam transmitted from the light-contacting portion to the light-collecting portion beneath the surface of the solid state rocket fuel; and wherein the internally transmitted beam is transmitted from the light-collecting portion of the surface and enters the collecting fiber light-entering end.

* * * * *